United States Patent [19]

Kleiner et al.

[11] Patent Number: 5,008,426
[45] Date of Patent: Apr. 16, 1991

[54] NOVEL 6-ACYL-(6H)-DIBENZ[C,E][1,2]OXAPHOSPHORIN 6-OXIDES, THEIR PREPARATION AND THEIR USE AS PHOTOINITIATORS

[75] Inventors: Hans-Jerg Kleiner, Kronberg; Joachim Gersdorf, Wiesbaden; Udo Bastian, Ratingen, all of Fed. Rep. of Germany

[73] Assignee: Hoechst Aktiengesellschaft, Frankfurt am Main, Fed. Rep. of Germany

[21] Appl. No.: 235,004

[22] Filed: Aug. 22, 1988

[30] Foreign Application Priority Data

Aug. 24, 1987 [DE] Fed. Rep. of Germany ....... 3728169
May 26, 1988 [DE] Fed. Rep. of Germany ....... 3817860

[51] Int. Cl.$^5$ .................. C07F 9/32; C09D 3/727; C08F 2/50; G03F 7/10
[52] U.S. Cl. .................................. 558/82; 252/600; 558/124; 430/281; 430/282; 430/285; 430/286; 430/288
[58] Field of Search ................................ 558/82, 124

[56] References Cited

U.S. PATENT DOCUMENTS

| | | |
|---|---|---|
| 3,562,361 | 2/1971 | Gier .................. 558/124 |
| 3,826,640 | 7/1974 | Theissen .................. 558/178 |
| 4,292,152 | 9/1981 | Lechtken et al. .................. 204/159.15 |
| 4,324,744 | 4/1982 | Lechtken et al. .................. 568/15 |
| 4,483,279 | 12/1969 | Davis et al. .................. 558/124 |
| 4,710,523 | 12/1987 | Lechtken et al. .................. 522/14 |

*Primary Examiner*—Mark L. Berch

[57] ABSTRACT

The invention relates 6-acyl-(6H)-dibenz[c,e][1,2]oxaphosphorin-6-oxides of the formula

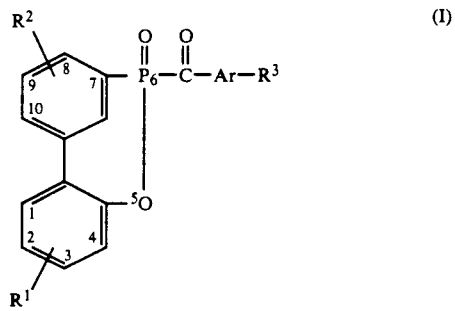

wherein each of $R^1$, $R^2$ and $R^3$ may be present one or more times and $R^1$, $R^2$ and $R^3$ represent halogen having an atomic number of from 9 to 35, alkyl or alkoxy each having from 1 to 6 carbon atoms and wherein Ar represents an aromatic hydrocarbon group having from 6 to 10 carbon atoms.

The invention further relates to a process for the preparation of the afore-mentioned compounds and polymerizable compositions containing them as an essential ingredient as a photo-initiator. Finally the invention relates to 6-alkoxy-(6H)-dibenz[c,e][1,2]oxaphosphorin of the formula II

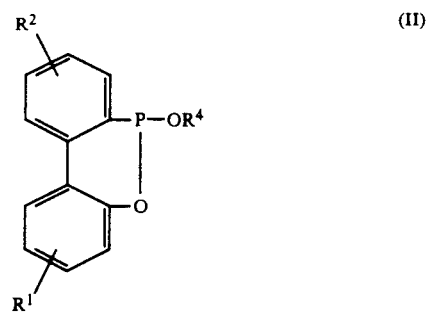

wherein each of $R^1$ and $R^2$ may be present once or more times and $R^1$ and $R^2$ represent halogen having an atomic number of from 9 to 35, alkyl or alkoxy each having from 1 to 6 carbon atoms, at least one $R^1$ being, however, halogen and wherein $R^4$ represents alkyl having from 1 to 6 carbon atoms.

17 Claims, No Drawings

NOVEL 6-ACYL-(6H)-DIBENZ[C,E][1,2]OXAPHOSPHORIN 6-OXIDES, THEIR PREPARATION AND THEIR USE AS PHOTOINITIATORS

DESCRIPTION

Novel 6-acyl-(6H)-dibenz[c,e][1,2]oxaphosphorin 6-oxides, their preparation and their use as photoinitiators.

The invention relates to novel 6-acyl-(6H)-dibenz[c,e]-[1,2]oxaphosphorin 6-oxides, their preparation and their use as photoinitiators in photopolymerizable compositions.

A number of photoinitiators based on acylphosphinates or acylphosphine oxides have already been disclosed (European Patent 7508). Phenyl acylphenylphosphinates, which come closest in structure to acyl-(6H)-dibenz[c,e][1,2]oxaphosphorin 6-oxides, are included in this patent specification as far as the structure is concerned. However, no details are presented therein on their synthesis and physical data. The related alkyl acylphenylphospinates and, in particular, acyldiphenylphosphine oxides can only be obtained via intermediates which are technically complicated to prepare (dichlorophenylphosphine or chlorodiphenylphosphine)

The invention has the object of providing novel acylphosphorus compounds which can be prepared in a technically particularly simple manner and, nevertheless, meet the high demands of industry.

The invention relates to 6-acyl-(6H)-[c,e][1,2]oxaphosphorin 6-oxides of the general formula I (see formula sheet) in which each of the radicals $R^1$, $R^2$ and $R^3$ may be present once or more times and $R^1$, $R^2$ and $R^3$ denote halogen having an atomic number from 9 to 35, alkyl or alkoxy each having 1 to 6, preferably 1 to 4, carbon atoms, and Ar denotes an aromatic hydrocarbon radical having 6 to 10 carbon atoms. Methyl and ethyl are particularly preferred as alkyl groups and methoxy is particularly preferred as alkoxy groups. In many cases, the compounds contain at least one chlorine atom, but expediently a maximum of two chlorine atoms, of which, in turn, at least one is expediently $R^3$. Each substituent $R^1$ and $R^2$ is expediently only present at most once, in particular as $R^1$, and is preferably not present at all.

In addition to the compounds, mentioned in the examples of the substances according to the invention, 6-(3-chlorobenzoyl)- and 6-(2,6-dichlorobenzoyl)-(6H)-dibenz[c,e][1,2]oxaphosphorin 6-oxide may be mentioned as examples, furthermore 6-benzoyl-(6H)-2- or -4-chloro-, 6-(2- or 3-methylbenzoyl)-(6H)-2- or -4-chloro, 6-(2,4- or 2,6- or 3,4- or 3,5-dimethylbenzoyl)-(6H)-2- or -4-chloro-, 6-(2,4,6-trimethylbenzoyl)-4-chloro-, 6-(2- or 3-chlorobenzoyl)-(6H)-2- or -4-chloro and 6-(2,6-dimethoxybenzoyl)-(6H) -2- or -4- chlorodibenz[cje][1,2]-oxaphosphorin 6-oxide.

The invention also relates to a process for the preparation of the 6-acyl-(6H)-dibenz[c,e][1,2]oxaphosphorin 6-oxides mentioned which comprises reacting 6-alkoxy(6H)-dibenz[c,e][1,2]oxaphosphorins of the general formula II (see formula sheet) with acyl chlorides of the general formula $Cl-CO-Ar-R^3$ (III) in which $R^1$, $R^2$, $R^3$ and Ar have the abovementioned meaning and $R^4$ denotes alkyl, expediently having 1 to 6 carbon atoms. In this reaction, the 6-acyl-(6H)-dibenz[c,e]-[1,2]oxaphosphorin 6-oxides of the formula I are obtained in good yields.

In the compounds of the formula II, $R^4$ preferably denotes methyl or ethyl, but may alternatively represent propyl, isopropyl or the various butyl, pentyl and hexyl radicals. In addition to methyl and ethyl or methoxy and ethoxy, the radicals $R^1$ and $R^2$ may, as alkyl, also contain the propyl, isopropyl, or one of the various butyl radicals.

The reaction may be carried out in the presence or absence of a catalyst, such as a tertiary amine, for example triethylamine or dimethylaniline, and in a solvent, such as a hydrocarbon or hydrocarbon mixture, such as petroleum ether, toluene, cyclohexane, an ether, such as dibutyl ether or tetrahydrofuran, or other customary organic solvents which are inert towards the reaction participants. However, the reaction without a solvent is preferred.

The reaction is expediently carried out by gradually metering in one of the components to the second, with alkyl chloride being eliminated. It is preferred to initially introduce the benzoyl chloride. The reaction is generally carried out at temperatures from 50° to 150° C., preferably 70° to 130° C., and in particular 80° to 120° C. The preparation is generally carried out at atmospheric pressure. However, since alkyl chloride is eliminated, it may be expedient to work at reduced pressure. In this case, it is preferred to use, at the reaction temperature used, a pressure such that the alkyl chloride is removed in vapour form and can be condensed per se. This simplifies work-up of the reaction product. The compounds of the formula I produced are purified, for example, by crystallization or distillation under reduced pressure, in particular in a high vacuum.

Some of the compounds of the general formula II used as starting materials are known. The new compounds are particularly those in which $R^1$ is halogen, in particular chlorine. The known compounds can be obtained smoothly from the corresponding 6-chloro-(6H)-dibenz[c,e][1,2]-oxaphosphorine. One synthetic route for these compounds of the general formula II which can also be used for the novel compounds is indicated on the formula sheet. Steps 1 to 2 can in practice be carried out in a one-pot process and thus combined. The process is described in principle in German Patent 2,034,887. In step 3 of this process, tertiary amines, such as triethylamine, are used and the reaction can be carried out at room temperature. It is obvious that this process is very simple to carry out in practice. The necessary formation of a P—C bond with formation of an arylphosphorus compound proceeds in a manner which is incomparably simple compared with the other known compounds.

The compounds according to the invention exhibit very good reactivity as photoinitiators for the photopolymerization of unsaturated compounds containing at least one C—C multiple bond and mixtures thereof with one another and with additives. Photopolymerizable mixtures of this type, as are used, for example, for the production of moldings such as printing plates and relief plates, contain, as essential components, at least one binder, at least one low-molecular-weight polymerizable monomer and at least one photoinitiator.

The photoinitiators according to the invention must be compatible with the monomers and soluble or dispersible in a suitable developer solvent in order to make it possible to wash out the unexposed and uncrosslinked parts of a coating of the photopolymerizable recording composition after imagewise exposure thereof.

Suitable photopolymerizable monomers are the customary compounds and substances containing polymerizable C—C double bonds which are activated, for example, by aryl, carbonyl, amino, amide, amido, ester, carboxyl or cyanide groups, halogen atoms or C—C double or C—C triple bonds. Vinyl ethers and vinyl esters, styrene, the various vinyl toluenes, acrylic acid and methacrylic acid, and the esters thereof with monohydric and/or polyhydric alcohols, the nitriles or amides thereof, mono- or diacrylates or -methyacrylates of oligomeric glycols, or acrylates and methacrylates of the products of the reaction of polyhydric alcohols with glycols, such as trimethylolpropane triethoxytriacrylate, maleates and fumarates and N-vinylpyrrolidone, N-vinylcaprolactam, N-vinylcarbazole and allyl esters, such as diallyl phthalate, may be mentioned as examples.

The binders may be saturated or unsaturated. Examples which may be mentioned are linear polyamides and, particularly, alcohol-soluble copolyamides, as described in French Patent 1,520,856, cellulose derivatives, in particular cellulose derivatives which can be washed out using aqueous alkaline media, vinyl alcohol polymers and polymers and copolymers of vinyl esters of saturated aliphatic monocarboxylic acids having 2 to 4 carbon atoms, such as vinyl acetate or vinyl propionate, with various degrees of hydrolysis, polyurethanes, polyether urethanes and polyester urethanes, and unsaturated polyester resins, as described below. Oligomeric or polymeric epoxy acrylates or epoxy methacrylates, prepared from acrylic acid or methacrylic acid and aromatic or aliphatic diglyceridyl ethers, urethane acrylates or methyacrylates (for example prepared from hydroxylalkyl acrylates or methacrylates and polyisocyanates), and polyester acrylates or methacrylates (for example prepared from hydroxyl group-containing saturated polyesters and acrylic acid or methyacrylic acid), polyester acrylates or methacrylates, prepared from diols of an aliphatic or aromatic nature and acrylic acid or methacrylic acid, amine acrylates or methacrylates and melamine acrylates or methacrylates (for example prepared from methylol derivatives of amines or of melamine and acrylic acid or methacrylic acid) are furthermore suitable.

Elastomeric block copolymers which contain at least two thermoplastic non-elastomeric polymer blocks having a glass transition temperature of above 25° C. and, between the non-elastomeric polymer blocks, an elastomeric polymer block having a glass transition temperature of less than 10° C. are furthermore suitable. Polystyrenepolyisoprene-polystyrene block copolymers, as described in U.S. Pat. No. 3,265,725, may be mentioned as examples.

It is also possible to replace the styrene components by polymers of homologues and analogues of styrene, such as α-methylstyrene and the various vinyl-toluenes.

if desired, the photopolymerizable compositions can be in the form of aqueous dispersions, or used in this form.

Saturated and/or unsaturated polymers and further additives, such as inhibitors against thermopolymerization, paraffin, pigments, dyes, peroxides, flow-control agents, fillers, flatting agents, glass fibers and stabilizers against thermal or photochemical degradation, may be added in a manner known per se to the photopolymerizable compositions whose composition is known to those skilled in the art for the particular application. The nature and quantity of the additives depends on the particular application.

The compounds according to the invention are generally employed in a concentration of 0.001 to 20, expediently 0.01 to 15 or 10%, preferably 0.1 to 5%, relative to the weight of the photopolymerizable composition. If desired, they may be combined with accelerators which eliminate the inhibiting influence of atmospheric oxygen on the photopolymerization. Such accelerators or synergists are above all, tertiary amines, such as methyl diethanolamine, dimethyl ethanolamine, triethylamine, triethanolamine, ethyl p-dimethylaminobenzoate, benzyl dimethylamine, dimethylaminoethyl acrylate, N-methyl-N-phenylglycine and analogous compounds known to those skilled in the art. In addition, aliphatic and/or aromatic halogen compounds, such as 2-chloromethylnaphthalene or 1-chloro-2-chloromethylnaphthalene and free radical generators, such as peroxides and azo compounds, may be used to accelerate curing.

According to a further advantageous embodiment, the compounds according to the invention may be employed in combination with other photoinitiators in all weight ratios, expediently from 0.5:1 to 30:1, preferably 0.8:1 to 10:1 and in particular 1:1 to 3:1. Suitable initiators of this type are, for example, aromatic ketones and functional derivatives thereof, such as ketals, for example benzyl dimethyl ketal, 2-hydroxy-2-methyl-1-phenylpropan-1-one, diethoxyacetophenone, benzophenone and derivatives of thioxanthone or mixtures of these. The total content of these combinations is generally between 1 and 20%, relative to the weight of the total polymerizable composition.

A particular advantage of these photoinitiator combinations is that the curing rate is thereby significantly increased and a better hardness of the cured films is achieved. A further advantage of the photoinitiator combinations is that the production costs for radiation-curable compositions entailed by the organophosporus compounds are significantly reduced.

A further, entirely unexpected advantage of the above-mentioned combination of known photoinitiators and photoinitiators according to the invention is that it is also possible to cure pigmented systems in coating thicknesses of well above 100 μm.

The curing rate can be further increased by adding secondary and/or tertiary amino compounds. For example, triethylamine, benzylmethylamine, benzyldimethylamine or those containing aliphatic hydroxyl groups, such as diethanolamine, N-methyldiethanolamine, phenyldiethanolamine, and the other abovementioned tertiary amino compounds, or mixtures thereof, are suitable.

The photoinitiators according to the invention may be combined with the known photoinitiators in a manner such that the appropriate emission region of the UV lamps corresponds fully to the absorption region of the initiator combination (for example 300–420 nm or 200–420 nm).

The recording compositions according to the invention predominantly, i.e. to more than 50 and preferably to 70 to 100% by weight, of the photoinitiator-containing mixture of monomers and binders. The content of polymeric binder in this mixture is generally about 45 to 90 and in particular 45 to 60% by weight, relative to the sum of the amounts of monomers and binders.

The processing of the photopolymerizable recording compositions into photopolymer printing plates can take place in a customary manner and is independent of whether the composition is liquid or solid. It takes place by imagewise exposure, for example with actinic light. To produce relief printing plates or photoresists, the unexposed parts of the coating of the recording compositions are then removed mechanically in the customary manner or washed out using a suitable developer solvent, and the resultant plates are dried, and in many cases also fully re-exposed.

It is particularly advantageous that, using the recording compositions, it is often possible to omit preexposure before imagewise exposure of coatings of these photopolymerizable recording compositions, good exposure times nevertheless being possible. An unexpected great advantage is furthermore that coatings of the recording compositions according to the invention produce improved relief structures when processed into relief printing plates, which results, for example, in significantly improved reproduction of reverse lettering during printing.

The radiation sources used for the light which initiates polymerization of such mixtures are advantageously those which emit light principally in the absorption region of the compounds according to the invention, i.e. between 200 or 300 and 450 nm. Low-pressure, medium-pressure and high-pressure mercury lamps and (superactinic) fluorescence tubes or impulse lamps are particularly suitable. The lamps mentioned may, if appropriate, be doped.

EXAMPLES

1. 6-Benzoyl-(6H)-dibenz[c,e][1,2]oxaphosphorin 6-oxide 56 g (0.399 mol) of benzoyl chloride were warmed to 80° to 85° C. under a nitrogen atmosphere. 92 g (0.4 mol) of 6-methoxy-(6H)-dibenz[c,e][1,2]oxaphosphorin were added dropwise over the course of 90 minutes while stirring. The temperature was then increased in steps to 130° C. It was kept at this temperature until evolution of methyl chloride could no longer be detected. The residue was digested with 70 ml of toluene at room temperature. 116 g (90% of theory) of the abovementioned compound, which, after rapid recrystallization from ethanol, had a melting point of 134° to 135° C.

$C_{19}H_{13}O_3P$ calc.: 71.25% C, 4.06% H, 9.69% P, (320) found: 71.2% C, 4.1% H, 9.5% P.

2. 6-(2-Methylbenzoyl)-(6H)-dibenz[c,e][1,2]oxaphosphorin 6-oxide 61.8 g (0.4 mol) of 2-methylbenzoyl chloride were warmed to 80° C. under a nitrogen atmosphere. 92 g (0.4 mol) of 6-methoxy-(6H)-dibenz[c,e][1,2]-oxaphosphorin were added dropwise over the course of two to three hours while stirring. The temperature was then increased in steps to 115° C. When the reaction was complete, 50 ml of acetone were added at room temperature. After crystallization, 103 g (77% of theory) of the above-mentioned compound of melting point 102° to 104° C. were obtained.

$C_{20}H_{15}O_3P$ calc.: 71.86% C, 4.49% H, 9.28% P, (334) found: 71.8%, C 4.42% H, 9.1% P.

3. 6-(3-Methylbenzoyl)-(6H)-dibenz[c,e][1,2]oxaphosphorin 6-oxide 46.6 g (0.3 mol) of 3-methylbenzoyl chloride were warmed to 85° C. under a nitrogen atmosphere. 69 g (0.3 mol) of 6-methoxy-(6H)-dibenz[c,e][1,2]-oxaphosphorin were added dropwise while stirring. The temperature was then increased in steps to 115° C. When the reaction was complete, 50 ml of toluene were added at room temperature. After crystallization, 85 g (84% of theory) of the abovementioned compound of melting point 108° to 111° C. were obtained.

$C_{20}H_{15}O_3P$ calc.: 71.86% C, 4.49% H, 9.28% P, (334) found: 71.9% C, 4.4% H, 9.2% P.

4. 6-(4-methylbenzoyl)-(6H)-dibenz[c,e][1,2]oxaphosphorin 6-oxide 30.8 g (0.2 mol) of 4-methylbenzoyl chloride were warmed to 80° C. under a nitrogen atmosphere. 46 g (0.2 mol) of 6-methoxy-(6H)-dibenz[c,e][1,2]-oxaphosphorin 6-oxide were added dropwise over the course of 1 hour while stirring. The temperature was then slowly increased to 110° C. When the reaction was complete, the residue slowly crystallized out at room temperature. 60 g (90% of theory) of the abovementioned compound, which, after recrystallization from toluene, had a melting point of 124 to 125% C. were obtained.

$C_{20}H_{15}O_3P$ calc.: 71.86% C, 4.49% H, 9.28% P, (334) found: 71.0% C, 4.6% H, 9.0% P.

5. 5-(4-tert.-Butylbenzoyl)-(6H)-dibenz[c,e][1,2]oxaphosphorin 6-oxide 39.2 g (0.2 mol) of 4-tert.-butylbenzoyl chloride were warmed to 80° C. under a nitrogen atmosphere. 46 g (0.2 mol) of 6-methoxy-(6H)-dibenz[c,e][1,2]oxaphosphorin 6-oxide were added dropwise with stirring. The temperature was then gradually increased to 120° C. When the reaction was complete, 45 ml of toluene were added. The product crystallized at room temperature. 52 g (70% of theory) of the abovementioned compound of melting point 151° to 155° C. were obtained.

$C_{23}H_{21}O_3P$ calc.: 73.40% C, 5.59% H, 8.25% P, (376) found: 73.4% C, 5.6% H, 8.1% P.

6. 6-(2,4-Dimethylbenzoyl)-(6H)-dibenz[c,e][1,2]oxaphosphorin 6-oxide 33.7 g (0.2 mol) of 2,4-dimethylbenzoyl chloride were warmed to 80° C. under a nitrogen atmosphere. 46 g (0.2 mol) of 6-methoxy-(6H)-dibenz[c,e][1,2]oxaphosphorin were added dropwise with stirring. The batch began to crystallize even during the addition. The temperature when then slowly increased to 135° C. with the proviso that toluene was added as diluent at 90° C. After digestion with toluene, 58 g (83% of theory) of the abovementioned compound of melting point 166° C. were obtained from the crystallizate.

$C_{21}H_{17}O_3P$ calc.: 72.41% C, 4.89% H, 8.91% P, (348) found: 72.3% C, 4.7% H, 8.8% P.

7. 6-(2,6-Dimethylbenzoyl)-(6H)-dibena[c,e][1,2]-oxaphosphorin 6-oxide.

16.85 g (0.1 mol) of 2,6-dimethylbenzoyl chloride were warmed to 80° C. under a nitrogen atmosphere. 23 g (0.1 mol) of 6-methoxy-(6H)-dibenz[c,e][1,2)oxaphosphorin were added dropwise while stirring. The temperature was slowly increased to 122° C. It was kept at this temperature until evolution of methyl chloride could no longer be detected. After cooling, 30 ml of toluene were added. After crystallization, 22.5 g (25% of theory) of the abovementioned compound, which had a melting point of 128° to 130° C., were obtained.

$C_{21}H_{17}O_3P$ calc: 72.41% C, 4.89% H, 8.91% P,
(348) found: 72.3% C, 4.7% H, 8.8% P.

8.
6-(3,4-Dimethylbenzoyl)-(6H)-dibenz[c,e[[1,2]oxaphosphorin 6-oxide 50.6 g (0.3 mol) of 3,4-dimethylbenzoyl chloride were warmed to 80° C. under a nitrogen atmosphere. 69 g (0.3 mol) of 6-methoxy-(6H)-dibenz[c,e][1,2]oxaphosphorin were added dropwise while stirring. Crystallization began even during the dropwise addition, and the temperature was therefore increased to 100° C.; at the same time, an additional 100 ml of toluene were added dropwise. When the dropwise addition was complete, the mixture was heated to reflux. When the reaction was complete and after crystallization, 87 g (83% of theory) of the abovementioned compound, which had a melting point of 160° to 162° C., were obtained.

$C_{21}H_{17}O_3P$ calc.: 72.41% C, 4.89% H, 8.91% P,
(348) found: 72.46% C, 4.8% H, 8.8% P.

9.
6-(3,5-Dimethylbenzoyl)-(6H)-dibenz[c,e][1,2]oxaphosphorin 6-oxide 67.4 g (0.4 mol) of 3,5-dimethylbenzoyl chloride were warmed to 80° C. under a nitrogen atmosphere. 92 g (0.4 mol) of 6-methoxy-(6H)-dibenz[c,e][1,2]oxaphosphorin were added dropwise while stirring. The temperature during the addition was increased in steps to 115° C. When the reaction was complete, 50 ml of acetone were added at room temperature. After crystallization, 113 g (81% of theory) of the abovementioned compound of melting point 120° to 124° C. were obtained.

$C_{21}H_{17}O_3P$ calc.: 72.41% C, 4.89% H, 8.91% P,
(362) found: 72.3% C, 4.8% H, 8.9% P.

10.
6-(2,4,6-Trimethylbenzoyl)-(6H)-dibenz[c,e][1,2]oxaphosphorin 6-oxide 18.25 g (0.1 mol) of 2,4,6-trimethylbenzoyl chloride were warmed to 85° C. under a nitrogen atmosphere 23 g (0.1 mol) of 6-methoxy-(6H)-dibenz[c,e][1,2]-oxaphosphorin were added dropwise while stirring. The temperature was slowly increased to 105° C. It was kept at this temperature until evolution of methyl chloride could no longer be detected. When the reaction was complete, toluene was added. After crystallization, 27 g (75% of theory) of the abovementioned compound of melting point 109° C. were obtained.

$C_{22}H_{15}O_3P$ calc.: 72.93% C, 5.25% H, 8.56% P,
(362) found: 72.7% C, 5.3% H, 8.3% P.

11.
6-(3-Methoxybenzoyl)-(6H)-dibenz[c,e][1,2]-oxaphosphorin 6-oxide.

42.6 g (0.25 mol) of 3-methoxybenzoyl chloride were warmed to 70° C. under a nitrogen atmosphere. 57.5 g (0.25 mol) of 6-methoxy-(6H)-dibenz[c,e][c,e]-oxaphosphorin were added dropwise while stirring. The temperature was then slowly increased to 120° C. It was kept at this temperature until evolution of methyl chloride could no longer be detected. After cooling to 90° C., 90 ml of toluene were added. After crystallization, 65 g (75% of theory) of the abovementioned compound of melting point 116° to 118° C. were obtained.

$C_{20}H_{15}O_4P$ calc: 68.57% C, 4.29% H, 8.86% P,
(350) found: 68.5% C, 4.3% H, 8.7% P.

12.
6-(2,4-Dimethoxybenzoyl)-(6H)-dibenz[c,e][1,2]oxaphosphorin 6-oxide 35.1 g (0.175 mol) of 2,4-dimethoxybenzoyl chloride were warmed to 70° C. under a nitrogen atmosphere. 40.3 g (0.175 mol) of 6-methoxy-(6H)-dibenz[c,e][1,2]oxaphosphorin were added dropwise in the course of two hours while stirring. The temperature was then slowly increased to 110° C. It was kept at this temperature until evolution of methyl chloride could no longer be detected. After cooling to 60° C., 70 ml of toluene were added. After crystallization, 50 g (75% of theory) of the abovementioned compound of melting point 112° to 115° C. were obtained.

$C_{21}H_{17}O_5P$ calc: 66.32% C, 4.47% H, 8.16% P,
(380) found: 66.3% C, 4.2% H, 8.0% P.

13.
6-(3,5-Dimethoxybenzoyl)-(6H)-dibenz[c,e][1,2]oxaphosphorin 6-oxide 35.1 g (0.175 mol) of 3,5-dimethoxybenzoyl chloride were warmed to 80° C. under a nitrogen atmosphere. 40.3 g (0.175 mol) of 6-methoxy-(6H)-dibenz[c,e][1,2]oxaphosphorin were added dropwise over the course of one hour while stirring. At the same time, the temperature was gradually increased to 115° C. When the reaction was complete, 60 ml of toluene were added at 80° C. After crystallization, 49 g (74% of theory) of the abovementioned compound of melting point 140° to 142° C. were obtained.

$C_{21}H_{17}/O_5P$ calc.: 66.32% C, 4.47% H, 8.16% P,
(380) found: 66.2% C, 4.5% H, 8.1% P.

14.
6-(2,6-Dimethoxybenzoyl)-(6H)-dibenz[c,e][1,2]oxaphosphorin 6-oxide 60.1 g (0.3 mol) of 2,6-dimethoxybenzoyl chloride were warmed to 85° C. under a nitrogen atmosphere. 69 g (0.3 mol) of 6-methoxy-(6H)-dibenz[c,e][1,2]oxaphosphorin were added dropwise while stirring. The temperature was then slowly increased to 125° C. When the reaction was complete and after cooling, 150 ml of toluene were added. After crystallization, 99 g (87% of theory) of the abovementioned compound of melting point 96° to 98° C. were obtained.

$C_{21}H_{17}O_5P$ calc.: 66.32% C, 4.47% H, 8.16% P,
(380) found: 66.1% C, 4.4% H, 8.2% P.

15.
6-(3,4,5-Trimethoxybenzoyl)-(6H)-dibenz[c,e][1,2]oxaphosphorin 6-oxide 35.6 g (0.154 mol) of 3,4,5-trimethoxybenzoyl chloride were warmed to 100° C. under a nitrogen atmosphere. 35.5 g (0.154 mol) of 6-methoxy-(6H)-dibenz[c,e][1,2]oxaphosphorin were then added dropwise while stirring, and the temperature was increased to 115° C. When the reaction was complete, 70 ml of toluene were added at 90° C., and the mixture was then cooled further. After crystallization, 44 g (70% of theory) of the abovementioned compound of melting point 147° to 149° C. were obtained.

$C_{22}H_{19}O_6P$ calc.: 64.39% C, 4.63% H, 7.56% P,
(410) found: 64.2% C, 4.4% H, 7.4% P.

16.
6-(2-Chlorobenzoyl)-(6H)-dibenz[c,e][1,2]oxaphosphorin 6-oxide 52.5 g (0.3 mol) of 2-chlorobenzoyl chloride were warmed to 80° C. under a nitrogen atmosphere. 69 g (0.3 mol) of 6-methoxy-(6H)-dibenz[c,e][1,2]oxaphosphorin were added dropwise while stirring. During the dropwise addition, the mixture was cooled to 60° C., and the temperature was then kept at 60°-70° C. When the reaction was complete, 40 ml of toluene were added at 45° C. 92 g (89% of theory) of the abovementioned compound of melting point 108° to 110° C. were obtained.

$C_{19}H_{12}ClO_3P$ calc.: 64.32% C, 3.39% H, 10.1% Cl, 8.75% P,
(354.5) found: 64.2% C, 3.4% H, 9.9% Cl, 8.6% P.

17.
6-(4-Chlorobenzoyl)-(6H)-dibenz[c,e][1,2]oxaphosphorin 6-oxide 35 g (0.2 mol) of 4-chlorobenzoyl chloride were warmed to 90° to 100° C. under a nitrogen atmosphere. 46 g of 6-methoxy-(6H)-dibenz[c,e][1,2]oxaphosphorin were added dropwise while stirring. The internal temperature was then increased gradually to 130° C. When the reaction was complete, the mixture was digested with 50 ml of toluene. 60 g (85% of theory) of the abovementioned substance of melting point 125° to 131° C. were obtained.

$C_{19}H_{12}Cl_1O_4P)$ calc.: 64.32% C, 3.39% H, 10.1% Cl, 8.75% P,
(354.5) found.: 64.1% C, 3.3% H, 9.7% Cl, 8.4% P.

18.
6-(2-Naphthoyl)-(6H)-dibenz[c,e][1,2]-oxaphosphorin 6-oxide 50 g (0.262 mol) of 2-naphthoyl chloride were warmed to 80° C. under a nitrogen atmosphere. 60.3 g (0.262 mol) of 6-methoxy-(6H)-dibenz[c,e][1,2]oxaphosphorin were added dropwise over the course of two hours while stirring. The internal temperature was subsequently increased gradually to 125° C. When the reaction was complete, 110 ml of toluene were added. After crystallization, 87 g (90% of theory) of the abovementioned compound of melting point 151° to 153° C. were obtained.

$C_{23}H_{15}O_3P$ calc.: 74.59% C, 4.05% H, 8.38% P,
(370) found: 74.5% C, 4.0% H, 8.2% P.

19.
6-(1-Naphthoyl)-(6H)-dibenz[c,e][1,2]oxaphosphorin 6oxide 50 g (0.262 mol) of 1-naphthoyl chloride were warmed to 80° to 85° C. under a nitrogen atmosphere. 60.3 g (0.262 mol) of 6-methoxy-(6H)-dibenz[c,e][1,-2]oxaphosphorin were added dropwise while stirring. The reaction proceeded exothermically. The temperature was then increased in steps to 125° C. When the reaction was complete, 90 ml of toluene were added at 40° C. After crystallization 77 g (80% of theory) of the above-mentioned compound of melting point 149° to 151° C. were obtained.

$C_{23}H_{15}O_3P$ calc.: 74.59% C, 4.05% H, 8.38% P,
(370) found: 74.4% C, 4.0% H, 8.1% P.

20.
6-(2-Methylnaphthoyl)-(6H)-dibenz[c,e][1,2]oxaphosphorin 6-oxide 96.7 g (0.473 mol) of 1-(2-methylnaphthoyl) chloride were warmed at 85° C. under a nitrogen atmosphere. 109 g (0.473 mol) of 6-methoxy-(6H)-dibenz[c,e][1,2]oxaphosphorin were added dropwise in the course of 2 to 3 hours while stirring. The internal temperature was subsequently increased gradually to 120° C. When the reaction was complete, the mixture was cooled to 50° C. and 100 ml of toluene were added. After crystallization, 142 g (78% of theory) of the abovementioned compound, which, after recrystallization from toluene, had a melting point of 155° to 156° C., were obtained.

$C_{24}H_{17}O_3P$ calc.: 75.00% C, 4.43% H, 8.07% P,
(384) found: 74.9% C, 4.4% H, 8.0% P.

21.
6-(4-Methylbenzoyl)-(6H)-2-chlorodibenz[c,e][1,2]oxaphosphorin 6-oxide (a) Preparation of 6-methoxy-(6H)-2-chlorodibenz[c,e][1,2]oxaphosphorin via three steps 1st step: dichloro(2-phenyl-4-chlorophenoxy)phosphine
79.5 g (0.389 mol) of 2-phenyl-4-chlorophenol were slowly heated to 150° C. with 65.7 g (0.478 mol) of phosphorus trichloride. Hydrogen chloride was evolved at the same time. When the reaction was complete, the mixture was distilled at 0.027 kPa. 80 g (67% of theory relative to the 2-phenyl-4-chlorophenol employed) of the abovementioned substance passed over at a temperature of 145° to 146° C. (see formula sheet, formula V where $R^1$=2-chloro and $R^2$=H)

$C_{12}H_8Cl_3OP$ calc.: 47.14% C, 2.62% H, 34.86Cl, 10.15% P,
(384) found: 47.0% C, 2.6% H, 34.3% Cl, 9.6% P.

2nd step:
6-chloro-(6H)-2-chlorodibenz[c,3][1,2]oxaphosphorin 165 g (0.54 mol) of dichloro-(2-phenyl-4-chlorophenoxy)phosphine and 1,1 g of anhydrous zinc chloride were warmed to 150° C.; the temperature was then increased in steps to 250° C. The mixture was then kept at this temperature until hydrogen chloride gas was no longer evolved. When the reaction was complete, the mixture was distilled at 0.027 kPa. 105 g (72.5% of theory) of the abovementioned substance of the formula VI (see formula sheet where $R^1$=-2-chloro and $R^2$=hydrogen) of solidification point 40.5° C. passed over at 160° C.

$C_{12}H_7Cl_2OP$ calc.: 53.53% C, 2.60H, 26.39% cl, 11.52P,
(269) found: 53.3% c, 2.9% H, 25.5% Cl, 11.5% P.

3rd step:
6-methoxy-(6H)-2-chlorodibenz[c,e][1,2]oxaphosphorin 94 g (0.349 mol) of 6-chloro-(6H)-2-chlorodibenz[c,e][1,2]oxaphosphorin were dissolved in 40 ml of toluene at 70° C. This solution was added dropwise over the course of 90 minutes from a heated dropping funnel to a mixture of 11.2 g (0.349 mol) of absolute methanol, 35.4 g (0.349 mol) of triethylamine and 150 ml of absolute toluene at 20° C. with cooling while stirring vigorously. The mixture was stirred at this temperature for a further 4 hours; the triethylamine hydrochloride was then filtered off under suction and washed with toluene.

The filtrate was freed from toluene in a waterpump vacuum and then distilled at 0.027 kPa. 72 g (78% of theory) of the abovementioned compound of formula II (see formula sheet where $R^1=$2-chloro, $R^2=$hydrogen and $R^4=$methyl) of melting point 46° to 49° C. passed over at 170° C.

$C_{13}H_{10}ClO_2P$ calc.: 58.98% C, 3.78% H, 13.42Cl, 11.72% P, (264.5) found: 58.9% C, 3.8% H, 13.3Cl, 11.4% P.

(b) Reaction according to the invention 17.8 g (0.115 mol) of 4-methylbenzoyl chloride were heated to 100° C. under a nitrogen atmosphere. 30.4 g (0.115 mol) of 6-methoxy-(6H)-2-chlorodibenz[c,e][1,2]oxaphosphorin were added dropwise from a heated dropping funnel while stirring. The temperature was increased gradually to 115° C. The mixture was kept at this temperature until methyl chloride was no longer evolved. When the reaction was complete, the residue was digested with 15–20 ml of toluene. 36 g (85% of theory) of the abovementioned compound of melting point 144° to 148° C. were obtained.

$C_{20}H_{14}ClO_3P$ calc.: 65.13% C, 3.80% H, 9.63Cl, 8.41% P, (368.5) found: 65.3% C, 3.9C H, 9.1% Cl, 7.6% P.

22.
6.(2,4,6-Trimethylbenzoyl)-(6H)-2-chlorodibenz[c,e][1,2]oxaphosphorin 6-oxide 22.8 g (0.125 mol) of 2,4,6-trimethylbenzoyl chloride were heated to 100° C. under a nitrogen atmosphere. 33.1 g (0.125 mol) of 6-methoxy-(6H)-2-chlorodibenz[c,e][1,2]oxaphosphorin were added dropwise while stirring. The temperature was slowly increased to 120° C. The mixture was kept at this temperature until methyl chloride was no longer evolved. After cooling, the residue was digested with acetone. 30 g (60% of theory) of the abovementioned compound of melting point 145° to 146° C. were obtained.

$C_{22}H_{18}ClO_3P$ calc.: 66.58% C, 4.54% H, 8,95% Cl, 7.82% P, (396.5) found: 66.6% C, 4.4% H, 8.8% Cl, 7.6% P.

23.
6-(4-Chlorobenzoyl)-(6H)-2-chlorodibenz[c,e][1,2]oxaphosphorin 6-oxide 16.1 g (0.092 mol) of 4-chlorobenzoyl chloride were warmed to 90° C. under a nitrogen atmosphere. 24.4 g (0.092 ) of 6 -methoxy-(6H)-2-chlorodibenz[c.e][1,2]-oxaphosphorin were added dropwise from heated dropping funnel while stirring. The temperature was increased gradually to 140° C. The mixture was kept at this temperature until methyl chloride was no longer evolved. After cooling, the residue was digested with 20 ml of toluene. 27 g (75% of theory) of the abovementioned compound of melting point 183° to 185° C. were obtained.

$C_{19}H_{11}Cl_2O_3P$ calc: 58.61% C, 2.83% H, 7.97% P, (389) found: 58.6% C, 2.8% H, 7.6% P.

USE EXAMPLES

24. A solution of 91.2 g of a styrene-isoprene-styrene three-block copolymer with a styrene content of 15%, 8 g of hexanediol-1,6-diacrylate, 0.5 g of 6-(2,4,6-trimethylbenzoyl)-(6H)-dibenz[c,e][1,2]oxaphosphorin 6-oxide and 0.3 g of 2,6-di-tert.-butyl-4-methylphenol in 100 g of toluene was cast onto a 125 μm thick, biaxially stretched and thermoset polyester film (polyethylene terephthalate) using a metal frame to form a 6 mm thick coating. After evaporation of the toluene, a 125 μm thick, biaxially stretched and thermoset polyester film (polyethylene therephthalate) provided with an adhesive coating was placed on the free surface of a 3 mm thick photopolymer coating, and the multilayered element was pressed for 5 minutes in a platen press at 110° C. using 2.8 mm thick spacers. After the uncoated polyester film had been peeled off, the photopolymer coating was exposed with a commercially available UV flat-plate exposure unit (emitted wavelength range 320–400 nm; intensity of the scattered UV light 14 mW/cm$^2$) for 220 seconds through the polyester film remaining and then for 15 minutes imagewise from the free coating side. After washing out the unexposed image points using tetrachloroethane, an elastic letterpress printing plate with good relief structuring (relief depth 1.0 mm) and a Shore A hardness of 63° was obtained.

25. 145.5 g of a copolymeric, internally plasticized poly(vinyl alcohol) (®Mowiol 04/M1 from Hoechst AG) were dissolved in 147 g of water by stirring at 90° C. After cooling to 70° C., 90 g of 2-hydroxyethyl methacrylate, 10 g of trimethylolpropane triacrylate, 5 g of 6-(2,4,6-trimethylbenzoyl)-(6H)-dibenz[c,e][1,2]oxaphosphorin 6-oxide and 1 g of 2,6-ditert.-butyl-4-methylphenol were added. The homogeneous viscous solution was applied as a coating to a 125 μm thick polyester film (polyethylene terephtalate) in a manner such that, after drying for 48 hours at room temperature, an approximately 1.2 mm thick, non-adhesive, photosensitive coating was produced. A 0.3 mm thick aluminum sheet provided with a polyurethane adhesive coat in accordance with German Offenlegungsschrift 1,597,515 was placed on the free coating surface, and the multi-layered element was pressed for 5 minutes in a platen press at 120° C. using 0.6 mm thick spacers. After the uncoated polyester film had been peeled off, the photosensitive coating was exposed imagewise for 5 minutes with a commercially available UV flat-plate exposure unit (wavelength range emitted 320 to 400 hm) intensity of the scattered UV light 10 mW/cm$^2$). After washing out the unexposed image points with warm water, a letterpress printing plate with good relief structuring and a Shore A hardness of 90° was obtained.

26. Photopolymer flexographic printing plates

A solution of 91 g of a styrene-isoprene-styrene three-block copolymer with a styrene content of 15%, 8 g of hexanediol 1,6-diacrylate, 0.3 g of 2,6-di-tert.-butyl-4-methylphenol and 1 g of 6-(2,4,6-trimethylbenzoyl)(6H)-dibenz[c,e][1,2]oxaphosphorin 6-oxide (Experiment A) or 1 g of 2,4,6-trimethylbenzoyldiphenylphosphine oxide (Comparison Experiment V 26.1) in 100 g of toluene was cast onto a 125 μm thick, biaxially stretched and thermoset polyester film (polyethylene terephtalate) using a metal frame to form a 6 mm thick coating. After evaporation of the toluene, the 3 mm thick polymer coating was pressed for 5 minutes at 110° C. in a platen press between two 125 μm thick, biaxially stretched and thermoset polyester films (polyethylene terephthalate) using 2.8 mm thick spacers. After the polyester films had been peeled off, the photopolymer coating was exposed for 30 minutes from each side using a commercially available UV flat-plate exposure unit (wavelength range determined 320–400 mm, intensity of the scattered UV light 14 mW/cm$^2$). The hardness was 65° C. Shore A for each of Experiment A and V 26.1, the modulus of elasticity (sample strips 150 mm in length and 15 mm in width, clamped length 100 mm) was 6.5N/mm$^2$ in Experiment A and 5.2N/mm$^2$ in V 26.1 (in each case the mean of five measurements, standard deviation ±0.3N/mm$^2$). Determination of the abrasion in accordance with DIN 53 516 gave 170.0±5.4 mg for Experiment A and 213.4±6.3 mg for V 26.1 (in each case the mean and standard deviation of 5 measurements).

Thus, a greater modulus of elasticity and a significantly greater abrasion resistance compared with the compound of V 26.1 was obtained at the same Shore A hardness for the compound according to the invention. The abrasion resistance is a measure of the press life to be expected for appropriate printing plates in the printing process.

27. and 28. Photopolymer planographic plates

27. A solution of 3.92 g of a copolymer of methyl methacrylate and methacrylic acid having the mean molecular weight 35,000 and the acid number 86, 3.92 g of trimethylolpropane triacrylate, 0.107 g of 6-(1-naphthoyl)(6H)-dibenz[c,e][1,2]oxaphosphorin 6-oxide, 0.084 g of the azo dye made from the diazonium salt of 2,4-dinitro-6-chlorobenzene and 2-methoxy-5-acetylamino-N-cyanoethyl-N-hydroxyethylaniline, and 0.07 g of 4-dimethylamino-4'-methyldibenzalacetone in 51.4 ml of 2-butanone was stirred, filtered and spin-coated on a plate whirler onto electrolytically roughened and anodized aluminum. The plates were dried for 2 minutes at 90° C.; the coating weight was 3.5 g/m$^2$. After applying a protective coating, the photopolymer coating was exposed under a combined negative original, comprising a half-tone step wedge, lines and 60- and 120-point grids, using an 8 kW xenon copying lamp. The exposed plate was developed for 1 minute using a developer comprising 3 parts by weight of sodium metasilicate×9 H$_2$O, 0.03 parts by weight of the product of the reaction of coconut fatty amine and ethylene oxide, and 96.97 parts by weight of demineralized water. The image was then fixed with 1% strength phosphoric acid and subsequently dyed using black fatty ink. A planographic printing plate with good resolution of the image points was obtained.

28. Example 27 modified by replacing the 0.107 g of 6-(1-naphthoyl)-(6H)-dibenz[c,e][1,2]oxaphosphorin 6-oxide by 0.21 g of 6-(2-methylnaphthoyl))-(6H)-dibenz[c,e][1,2]oxaphosphorin 6-oxide and omitting the addition of the 4-dimethylamino-4'-methyldibenzalacetone. A planographic printing plate with good resolution of the image points was again obtained.

29. Dry photoresist plate

A solution of 27.5 g of a terpolymer made from n-hexyl methacrylate, methacrylate acid and styrene (60:30:10) and having a mean molecular weight of 35,000 and the acid number 195, 18.3 g of trimethylolpropane triacrylate, 0.92 g of 6-(1-(2-methylnaphthoyl))-(6H)-dibenz[c,e][1,2]oxaphosphorin 6-oxide and 0.05 g of the azo dye made from the diazonium salt of 2,4-dinitro-6-chlorobenzene and 2-methoxy-5-acetylamino-N-cyanoethyl-N-hydroxyethylanilin in 92.8 ml of butanone and 2 ml of ethanol was spin-coated onto a biaxially stretched and thermoset polyethylene terephthalate film of thickness 25 μm in a manner such that a coating thickness of 35 μm was obtained after drying at 110° C. A dry resist film was obtained which was laminated with a commercially available laminator at 120° C. onto a laminated phenoplast sheet coated with a 35 μm thick copper foil, and exposed imagewise for 90 seconds with an 8 kW xenon copying lamp. The original used was a line original with line widths and separations down to 80 μm. After exposure, the polyester film was removed and the coating was developed by spraying with a 1% strength sodium carbonate solution for 2 minutes. The sheet was then dipped into 15% strength ammonium peroxydisulfate solution at 50° C. The copper surfaces corresponding to the unexposed parts of the coating were removed by etching, and the exposed coating remaining was removed using trichloroethane, after which a flaw-free negative copper image of the image original was obtained.

30–47. Pigmented UV thick-layer casting compositions

Various pigmented thick-layer casting compositions based on a combination of ethoxy acrylates of the following composition were investigated:

| | |
|---|---|
| (a) epoxyacrylate prepolymer | 77.5 parts by wt. |
| (b) tripropylene glycol diacrylate | 2.5 |
| (c) dipropylene glycol diacrylate | 20.0 |
| (d) pigment | 0.1–5 |
| (e) photoinitiator mixture | 5.0 |

The epoxy acrylate prepolymer component comprised a combination of 4 different types, namely ®Roskydal LS 2812 (maximum acid number 5, maximum OH number 300, viscosity 300 Pa.s) from Bayer AG, Leverkusen, Germany, ®Setacure AP 569 (maximum acid number 5, viscosity 100–150 Pa.s) from Synthese-Chemie, Bergen op Zoom, Netherlands, ®Ebecryl 600 (aromatic bisphenol A acrylate, maximum acid number 8, molecular weight 500, viscosity 4000–8000 mPa.s) and Ebecryl 170 PA, both from UCB in Drogenbos, Belgium, in the weight ratio 40:20:10:7.5. The first three types are neutral epoxy acrylate prepolymers. Ebercryl 170 PA is a carboxyl group-containing prepolymer. The pigments employed were various products, such as ®Heliogen blue (BASF AG, Ludwigshafen, Germany), carbon black, titanium dioxide, iron oxide, ®Hostaperm yellow, Hostaperm scarlet GO. The photoinitiator mixture comprised equal parts of 2-hydroxy-2-methylpropiophenone and an acylphosphine oxide, to be precise the individual substances listed in Examples 2 to 4, 6, 8 to 17, 19 and 21 to 23.

The pigmented thick-layer casting compositions were applied to an aluminum substrate in coating thicknesses from 100–5000 μm. Curing was effected under a Hg high pressure lamp (80 W/cm) for 5–10 minutes, depending on the coating thickness and the pigment. Casting compositions with a bright surface, good adhesion and high chemical resistance were produced.

48. Highly pigmented UV top coats

In the recipe given in Examples 40–47, the pigment proportion can be increased to 30–60%. The paints produced in this case were applied in coating thicknesses from 5–100 μm and cured in a IV tunnel dryer with Hg high-pressure lamps (2×20 cm-10 w/cm) at a passage speed between 1 and 10 m/min, which was adjusted depending on the coating thickness and the type of pigment. Application took place by knife coating or rolling. By adding solvents (adjustment to a solids content of about 70%), it was also possible to process the paint material by spraying, for example for the production of coatings on glass, polyester films, various metal substrates, etc.

49.–66. Highly pigmented UV paints for dab printing or screen printing

Pigmented paints for dab printing or screen printing, comprising

| (a) epoxyacrylate prepolymers (Roskydal LS 2812). | 35.0 parts by wt |
|---|---|
| (b) hexanediol diacrylate | 16.0 parts by wt |
| (c) titanium dioxide | 50.0 parts by wt |
| (d) photoinitiator combination (as in Examples 30 to 47) | 5.0 parts by wt | were investigated. The paint films were aired in a UV tunnel dryer at a passage speed of 1–15 m/min, which was adjusted depending on the coating thickness and type of pigment, by 2 Hg high-pressure lamps (2×20 cm–100 W/cm).

Application was effected, for example, by printing polyester films, polycarbonate, various metal substrates, etc.

67.–84. Highly pigmented and clear UV matt paints

Paints based on a somewhat different combination of epoxy acrylates as in Examples 30 to 47 were investigated. The paint system comprised

| (a) epoxyacrylate prepolymers | 72.5 parts by wt. |
|---|---|
| (b) tripropylene glycol diacrylate | 7.5 parts by wt. |
| (c) dipropylene glycol diacrylate | 20.0 parts by wt. |
| (d) flatting agent | 5.0 parts by wt. |
| (e) pigment (as in Examples 30–47) | 10.0 parts by wt. |
| (f) photoinitiator combination (as in Examples 30 to 47) | 5.0 parts by wt. |

The epoxy acrylate prepolymer component comprised a combination of Roskydal LS 2812, Setacure AP 569, Ebercryl 170 PA and Ebercryl 600 in the weight ratio 40:20:10:2.5. The flatting agent used was ®Pergopak M, a urea-formaldehyde condensation product, from Martinswerk GmbH, Bergheim/Erft, Germany.

Glass surfaces and polyester films were coated with this paint system and cured in a UV tunnel dryer at a passage speed of 5–10 m/min, again depending on the type of pigment and the coating thickness (2 Hg high-pressure lamps of length 20 cm; 100 W/cm).

85.–102. UV filler compositions

UV-curable, styrene-free filler compositions with a high filler content which are suitable, for example, for automobile repair and are based on the following recipe were investigated:

| (a) epoxyacrylate prepolymer | 36.25 parts by wt. |
|---|---|
| (b) tripropylene glycol diacrylate | 3.75 parts by wt. |
| (c) dipropylene glycol diacrylate | 10.0 parts by wt. |
| (d) activated silica C ® Aerosil 300) | 1.0 parts by wt. |
| (e) iron oxide ( ® Bayferrox 316) | 0.07 parts by wt. |
| (f) titanium dioxide | 2.1 parts by wt. |
| (g) talc (Finntalc M 40) | 38.5 parts by wt. |
| (h) photoinitiator combination (as in Examples 30 to 47) | 4.5 parts by wt. |

The epoxyacrylate prepolymer component comprised Roskydal LS 2812, Setacure AP 570 (maximum acid number 4, viscosity 80–120 Pa.s), Ebercryl 170 PA and Ebecryl 600 in the weight ratio 20:10:5:1.25.

The compositions were applied to metal and cured for 10–15 minutes using Hg high-pressure lamps (400 W). After UV curing, it was possible to grind the coatings both in the wet and the dry state.

103. UV varnishes

The pigments (components (d) to (g)) in the recipe given in Examples 85 to 102 were omitted, and varnishes were thus produced. A significant increase in the curing rate and in the hardness of the coatings was observed.

104.–107. Pigmented paints for wood materials and furniture

A mixture of the photoinitiators 6-(2,4,6-trimethylbenzoyl)-(6H)-dibenz[c,e][1,2]oxaphosphorin 6-oxide (Example 10) and 2-hydroxy-2-methyl-1-phenylpropan-1-one was tested in various synthetic resins. To this purpose, the product of Example 10 was dissolved in the 2-hydroxy-2-methyl-1-phenylpropan-1-one on a hot water bath (80°–90° C.) to give a 50% strength solution. This solution remained clear during the processing time of several days at 20°–25° C.

Experimental paints were then produced from the following components:

| synthetic resin | 76.5 parts by wt. |
|---|---|
| (R)Bayertitan RKB 3 (pigment) | 9.0 parts by wt. |
| tripropylene glycol diacrylate | 10.0 parts by wt. |
| Initiator mixture | 4.5 parts by wt. |

The synthetic resins employed were those from Vianova Kunstharz AG, Werndorf bei Graz, Austria; an epoxy acrylate (Viaktin VTE 5940) in Example 104, an epoxy acrylate (Viaktin VTE 5286) in Example 105, a melamine acrylate (Viaktin VTE 5956) in Example 106, an unsaturated polyester (Viapal UP 586 E) in Example 107.

Viaktin VTE 5940 is a UV-curable, pre-sensitized, acrylic-modified epoxy resin, 80% strength in hexanediol 1,6-diacrylate, of dynamic viscosity/25° C. of 7000–11,000 mPa.s, colour index in accordance with DIN 6162 of less than 7 and acid number in accordance with DIN 53402 of less than 17. Viaktin VTE 5286 is an electron beam-curable, acrylic-modified epoxy resin, 80% strength in hexandiol 1,6-diacrylate, which has the same characteristic numbers as Viaktin VTE 5940. Viaktin VTE 5956 is a non-UV-presensitized 100% strength melamine acrylate of dynamic viscosity/25° C. of 400–2000 mPa.s and maximum color index in accordance with DIN 6162 of 1. Viapal UP 586 U is a photopolymerizable unsaturated glossy polyester resin (67% strength in styrene, of dynamic viscosity/20° C. of 750–1000 mPa.s, color index in accordance with DIN 6162 of less than 2 and acid number in accordance with DIN 63 402 of less than 30.

The paints were applied using a hand-knife coater
(a) onto glass in coating thicknesses of 30 μm and 60 μm
(b) in order to test the Erichsen cupping onto original Erichsen sheets in coating thicknesses of 30 μm and 60 μm.

Curing took place by irradiation with a UV high-pressure lamp (lamp power 80 Watt/cm) at a feed rate of 0.5 m/min.

The films were then tested for pendulum damping by the method of Persoz in accordance with the French standard NFT 30016, Erichsen cupping in accordance with DIN 53 156 and for chemical resistance. For the last-mentioned test, they were exposed for 5 minutes each to (a) a mixture of equal parts by weight of ethanol and water, (b) acetone, (c) methyl ethyl ketone (MEK) and (d) equal parts by weight of isopropanol and water, and for 30 minutes to water. The results are collated in the table below. It can be seen that good curing took place.

| | Results (measured data) | | | | | | | | |
|---|---|---|---|---|---|---|---|---|---|
| | Persoz pendu- lum hardness | | Erichsen cupping | | Chemical tests 30 μm | | | | |
| Ex- ample | 30 μm | 60μm | 30 μm | 60 μm | ethanol 50% strength | Ace- tone | MEK | Isopropanol 50% strength | Water |
| 104 | 298 | 243 | 1.7 | 1.3 | OK | OK | OK | OK | OK |
| 105 | 307 | 305 | 1.5 | 1.3 | OK | OK | OK | OK | OK |
| 106 | 329 | 308 | 1.2 | 0.9 | OK | OK | OK | OK | OK |
| 107 | 240 | 229 | 3.2 | 2.0 | OK | OK | OK | OK | OK |

Formula Sheet

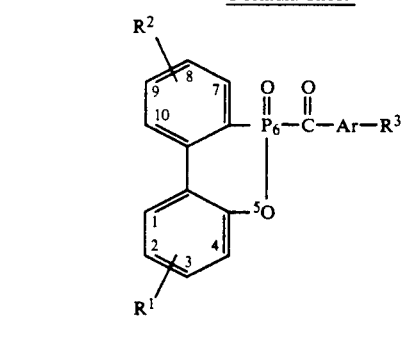

(I)

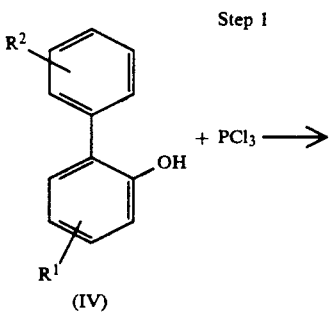

Step 1

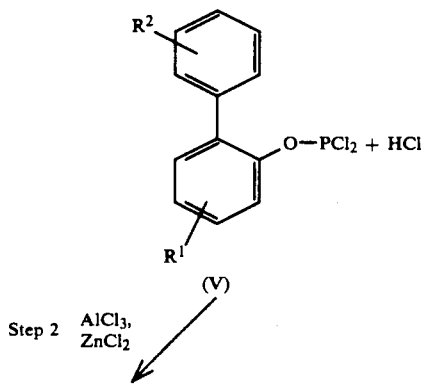

Step 2  AlCl₃, ZnCl₂

-continued
Formula Sheet
Step 3

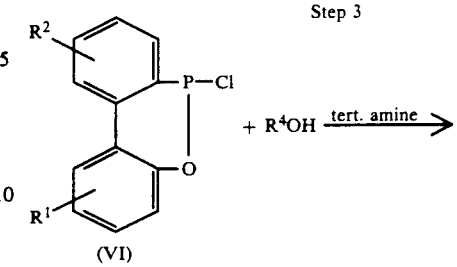

+ R⁴OH $\xrightarrow{\text{tert. amine}}$

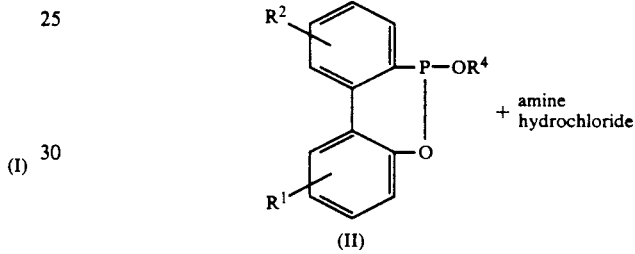

+ amine hydrochloride (II)

We claim:
1. A 6-acyl-(6H)-dibenz(c,e)(1,2)-oxaphosphorin-6-oxide of the formula

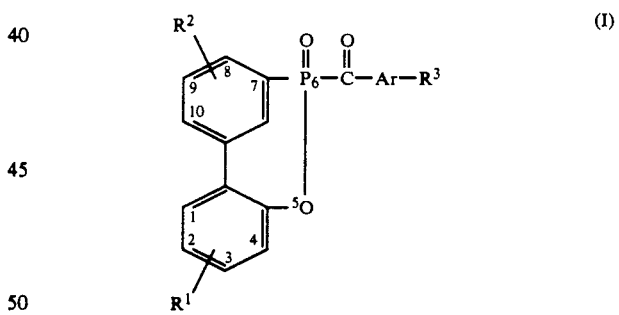

(I)

wherein each of $R^1$, $R^2$ and $R^3$ are present once or more than once, wherein $R^1$ and $R^2$ represent hydrogen or chlorine, $R^3$ represents hydrogen, chlorine or alkyl or alkoxy each having from 1 to 6 carbon atoms and wherein Ar represents an aromatic hydrocarbon group having from 6 to 10 carbon atoms.

2. A compound as claimed in claim 1, wherein at least one of $R^1$, $R^2$ and $R^3$ represents chlorine.

3. A compound as claimed in claim 2, wherein $R^1$, $R^2$ and $R^3$ altogether contain at most two chlorine atoms.

4. A compound as claimed in claim 3, wherein at least one chlorine atom is present as $R^3$.

5. A compound as claimed in claim 1, wherein alkyl and alkoxy each contain from 1 to 4 carbon atoms.

6. A compound as claimed in claim 5, wherein alkyl represents methyl or ethyl and wherein alkoxy represents methoxy.

7. A compound as claimed in claim 1, which contains at most one group $R^1$ and at most one group $R^2$, wherein both $R^1$ and $R^2$ are different from hydrogen.

8. A compound as claimed in claim 7, wherein $R^1$ and $R^2$ are both hydrogen.

9. A compound as claimed in claim 1, which contains at least one group $R^3$ and at most 3 groups $R^3$, wherein $R^3$ is different from hydrogen.

10. A compound as claimed in claim 9, in which one of the group $R^3$ is in ortho-position to the bond of the carbonyl group and any further $R^3$ groups are in ortho-position or para-position or both and where $R^3$ is different from hydrogen.

11. A 6-acyl-(6H)-dibenz(c,e)(1,2)-oxaphosphorin-6-oxide of the formula

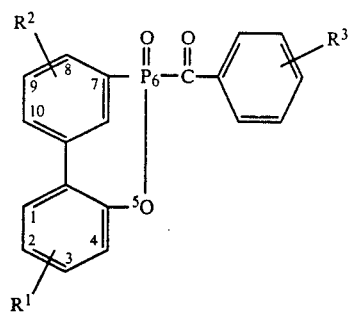

wherein each of $R^1$, $R^2$ and $R^3$ are present once or more than once, wherein $R^1$ and $R^2$ represent hydrogen or chlorine and $R^3$ represents hydrogen, chlorine or alkyl or alkoxy each having from 1 to 6 carbon atoms.

12. A compound as claimed in claim 11, wherein at least one of $R^1$, $R^2$ and $R^3$ represents chlorine.

13. A compound as claimed in claim 11, wherein alkyl and alkoxy each contain from 1 to 4 carbon atoms.

14. A compound as claimed in claim 13, wherein alkyl represents methyl or ethyl and wherein alkoxy represents methoxy.

15. A compound as claimed in claim 11, which contains at most one group $R^1$ at most one group $R^2$, wherein both $R^1$ and $R^2$ are different from hydrogen.

16. A compound as claimed in claim 15, which contains at least one group $R^3$ and at most 3 groups $R^3$, wherein $R^3$ is different from hydrogen.

17. A compound as claimed in claim 16, which contains a group $R^3$ in a position ortho to the bond of the carbonyl group and in addition at least one group $R^3$ in the other ortho-position or the para-position and wherein $R^3$ is different from hydrogen.

* * * * *